US011793905B2

(12) United States Patent
Grover et al.

(10) Patent No.: US 11,793,905 B2
(45) Date of Patent: Oct. 24, 2023

(54) DRESSING (71) Applicant: University of Birmingham, Birmingham (GB)

(72) Inventors: Liam Grover, Birmingham (GB); Ann Logan, Birmingham (GB); Felicity De Cogan, Birmingham (GB); Gurpreet Chouhan, Birmingham (GB)

(73) Assignee: THE UNIVERSITY OF BIRMINGHAM, Birmingham (GB)

( * ) Notice: Subject to any disclaimer, the term of this patent is extended or adjusted under 35 U.S.C. 154(b) by 0 days.

(21) Appl. No.: 16/540,142

(22) Filed: Aug. 14, 2019

(65) Prior Publication Data
US 2020/0038544 A1 Feb. 6, 2020

Related U.S. Application Data (63) Continuation of application No. 15/542,865, filed as application No. PCT/GB2016/050061 on Jan. 11, 2016, now abandoned.

(30) Foreign Application Priority Data

Jan. 12, 2015 (GB) ...................................... 1500430

(51) Int. Cl.
*A61L 15/28* (2006.01)
*A61L 15/44* (2006.01)
*A61L 27/34* (2006.01)
*A61L 27/54* (2006.01)

(52) U.S. Cl.
CPC .............. *A61L 15/28* (2013.01); *A61L 15/44* (2013.01); *A61L 27/34* (2013.01); *A61L 27/54* (2013.01); *A61L 2300/252* (2013.01); *A61L 2300/258* (2013.01); *A61L 2300/40* (2013.01); *A61L 2300/416* (2013.01)

(58) Field of Classification Search
CPC .......... A61L 15/28; A61L 15/44; A61L 27/34; A61L 27/54; A61L 2300/416; A61L 2300/258; A61L 2300/252; A61L 2300/40
See application file for complete search history.

(56) References Cited

U.S. PATENT DOCUMENTS

| 5,851,994 | A | 12/1998 | Schreiber | |
| 2005/0129771 | A1 | 6/2005 | Asgharian | |
| 2008/0132991 | A1* | 6/2008 | Pinchuk | A61L 31/10 623/1.13 |
| 2013/0296761 | A1* | 11/2013 | Goto | A61K 9/0014 602/54 |
| 2015/0044259 | A1 | 2/2015 | Desilva | |

FOREIGN PATENT DOCUMENTS

| EP | 0454373 | 4/1991 |
| EP | 0454373 | 10/1991 |
| JP | 2002-104974 | 4/2002 |
| JP | 2002104974 | 4/2002 |
| TW | 201225992 | 7/2012 |
| WO | 2001/002477 | 1/2001 |
| WO | 2001002477 | 1/2001 |
| WO | 2006/037606 | 4/2006 |
| WO | 2006037606 | 4/2006 |
| WO | 2008/067518 | 6/2008 |
| WO | 2008067518 | 6/2008 |
| WO | 2012/054301 | 4/2012 |
| WO | 2012054301 | 4/2012 |
| WO | 2014/130411 | 8/2014 |
| WO | 2014130411 | 8/2014 |

OTHER PUBLICATIONS

Scott, et al. JBC vol. 281, No. 19, pp. 13324-13332, May 12, 2006 (Year: 2006).*
PCT Search Report prepared for PCT/GB2016/052166, dated Nov. 11, 2016.
Paderi, J. E., & Panitch, A. (2008). Design of a synthetic collagen-binding peptidoglycan that modulates collagen fibrillogenesis. Biomacromolecules, 9(9), 2562-2566.
Zhang, Z., Garron, T. M., Li, X. J., Liu, Y., Zhang, X., Li, Y. Y., & Xu, W. S. (2009). Recombinant human decorin inhibits TGF-β 1-induced contraction of collagen lattice by hypertrophic scar fibroblasts. Burns, 35(4), 527-537.
Reese, S. P., Underwood, C. J., & Weiss, J. A. (2013). Effects of decorin proteoglycan on fibrillogenesis, ultrastructure, and mechanics of type I collagen gels. Matrix Biology, 32(7), 414-423.
Zhang, Z., Garron, T., Li, X. J., Liu, Y., Zhang, X., Li, Y. Y., & Xu, W. S. (2009). Recombinant Human Decorin Inhibits TGF-b1 Induced Contraction of Collagen Lattice by Keloid Fibroblasts. Wounds: a compendium of clinical research and practice, 21(2), abstract.
Park, H., Karajanagi, S., Wolak, K., Aanestad, J., Daheron, L., Kobler, J. B., . . . & Zeitels, S. M. (2009). Three-dimensional hydrogel model using adipose-derived stem cells for vocal fold augmentation. Tissue Engineering Part A, 16(2), 535-543.
Chouhan, G., Logan, A., Rauz, S., Scott, R. A., De Cogan, F., & Grover, L. M. (2015). Development of a synthetic anti-scarring dressing for the prevention of corneal scarring. Investigative Ophthalmology & Visual Science, 56(7), Abstract.
Qi, D., Zhou, Y., & Zhang, X. (2015). Advances in the research of modulation of dermal collagen fibrin assembly by decorin. Chinese journal of burns, 31(2), abstract.
EP Search Report prepared for GB1512582.6, dated Apr. 26, 2016.
Hill, Lisa J., et al. "Decorin reduces intraocular pressure and retinal ganglion cell loss in rodents through fibrolysis of the scarred trabecular meshwork." Investigative ophthalmology & visual science 56.6 (2015): 3743-3757.

(Continued)

*Primary Examiner* — H. Sarah Park (74) *Attorney, Agent, or Firm* — Brannon Sowers & Cracraft PC (57) ABSTRACT

The invention relates to a surgical or wound dressing comprising a sheet of gellan gum and an antifibrotic agent. Methods of producing dressings comprising gellan gums and biologically active agents area also produced.

20 Claims, 7 Drawing Sheets

(56) References Cited

OTHER PUBLICATIONS

Botfield, Hannah, et al. "Decorin prevents the development of juvenile communicating hydrocephalus." Brain 136.9 (2013): 2842-2858.

Logan, Ann, Andrew Baird, and Martin Berry. "Decorin attenuates gliotic scar formation in the rat cerebral hemisphere." Experimental neurology 159.2 (1999): 504-510.

Search Report prepared for GB 1500430.2, dated Jun. 20, 2015.

PCT Search Report prepared for PCT/GB2016/050061, dated Jul. 11, 2016.

Search Report prepared for GB 1500430.2, dated Jun. 30, 2015.

Zhang, Z., Garron, T., Li, X. J., Liu, Y, Zhang, X., Li, Y. Y., & Xu, W. S. (2009). ❐ ❐ Recombinant Human Decorin Inhibits TGF-b1 Induced Contraction of Collagen Lattice by Keloid Fibroblasts. Wounds: a compendium of clinical research and practice, 21(2), 47-56, abstract, 2009.

Chouhan, G., Logan, A., Rauz, S., Scott, R. A., De Cogan, F., & Grover, L. M. (2015). Development of a synthetic anti-scarring dressing for the prevention of corneal scarring. Investigative Ophthalmology & Visual Science, 56(7), 2471, Abstract.

Qi, D., Zhou, Y., & Zhang, X. (2015). Advances in the research of modulation of dermal collagen fibrin assembly by decorin. Chinese journal of burns, 31 (2), 157-159, abstract.

Scott, P. G., Dodd, C. M., Bergmann, E. M., Sheehan, J. K., & Bishop, P. N. (2006). Crystal structure of the biglycan dimer and evidence that dimerization is essential for folding and stability of class I small leucine-rich repeat proteoglycans. Journal of Biological Chemistry, 281(19), 13324-13332.

* cited by examiner

DRESSING

CROSS-REFERENCE TO RELATED APPLICATION

This application is a continuation of U.S. patent application Ser. No. 15/542,865, filed Jul. 11, 2017, which is a U.S. national entry application under 37 C.F.R. § 371(b) of International Application Serial No. PCT/GB2016/050061 filed Jan. 11, 2016, which claims the right of priority and benefit under 35 U.S.C. §§ 119 & 365 of GB Patent Application No. 1500430.2 filed on Jan. 12, 2015, the disclosures of which are incorporated herein by reference in their entirety.

The invention relates to a dressing, and in particular a surgical/wound dressing, comprising a sheet of gellan gum. The gellan gum may comprise one or more biologically active additives, such as an antifibrotic agent. Methods of producing the dressings and additionally the uses of the dressing are also provided. The dressings may be used, for example but not exclusively, to reduce scarring in burns, wounds, surgical and ophthalmic treatments.

The use of wound dressings is generally known in the art. A particular problem associated with many wounds, such as those from ophthalmic surgery or burns, is that such wounds often produce scarring. Scars are typically areas of fibrous tissue (fibrosis) that replace normal skin after injury. Scar tissue typically comprises a range of extracellular matrix molecules including collagen, but the fibre composition of the matrices is often different from that of normal tissue. Instead of a random basket weave formation of the fibres found in normal tissue, in fibrosis the fibres cross-link and forms a pronounced alignment in a single direction. This collagenous scar tissue alignment is usually of inferior functional quality to the normal randomised fibre alignment found in normal tissue. This means that the wound, when it heals, often has reduced or impaired mechanical properties, as well as having an adverse visual appearance.

Currently it is known that where corneal tissue damage has occurred, for example, due to injury to the eye or surgery to the eye, it is possible to apply amniotic membrane from the placenta of mammals to the cornea. This is not ideal due to ethical issues, the potential to contain pathogens and moreover it is often difficult to procure in large quantities and to be of reproducible quality.

There is therefore the need for a membrane which may be applied to wounds, such as in the cornea and skin. The addition of antifibrotic material, such as decorin, allows the amount of scarring to be controlled or reduced.

Membranes for use in the treatment of wounds and to encourage new skin growth are generally known in the art. For example, U.S. Pat. No. 4,983,181 describes a collagen hydrogel for promoting epithelial growth. Some problems with such gels is that they are relatively mechanically weak and they have a tendency to contract and degrade. Cellulose based membranes, such as US 2012/0231038, have also been generally described. Gums such as alginates have previously been described for the topical delivery of drugs (WO 2013/079605) but have inferior mechanical properties. Additionally, polymer gels have also been described as ways of producing cell delivery systems (WO 2014/140549). In the latter case, a range of different polymer gels are described, with agrose being particularly exemplified. Cells are suspending within a liquid phase with a plurality of polymer gels particulates. That gel is then applied to an area to be treated.

Gellan is a generally known polysaccharide gum which is produced by a *Pseudomonas elodea*. This is a hydrocolloid manufactured by fermentation from a carbohydrate source. Deacylation is carried out by treating the product with alkali.

Gellan gum is based on a linear structure of repeating, glucose, rhamnose and glucuronic acid units. In high acyl gellan gum, two acyl side chains, of acetate and glycerate, are present. Both substituents are present on the same glucose molecule and on average there is one glycerate per repeating unit and one acetate every two repeating units. In low acyl gellan gum the acyl groups are removed. High acyl products tend to form soft elastic gels while low gellan gum produces firmer, less elastic gels.

The Applicants have found that it is possible to produce thin sheets of gellan gum. These are more resistant than materials like alginates and collagen. Moreover, they are relatively transparent which allows the wound to be viewed through the gellan material. Additionally, the gellan sheet may conveniently be dried to allow the material to be stored, prior to the addition of suitable aqueous liquid to rehydrate them prior to use.

Gellan has also been found to have the additional advantage of being able to readily incorporate one or more biologically active ingredients, such as antifibrotic agents. When applied to wounds, this dressing has been found to improve the ability to reduce scarring.

Transforming growth factor-beta (TGF-β) is known to affect the process of wound healing during various phases, including that of wound contraction. It augments fibroblast contraction of collagen gels in vitro and enhances the wound contraction process in vivo, possibly by increased synthesis of actin, fibronectin and matrix receptors. Decorin is a secreted 45 kDA proteoglycan with a core protein comprising primarily leucine-rich repeats and is found in the extra cellular matrix of several tissues such as skin, ocular fluids, cartilage and bone. Decorin has been found to bind TGF-β and neutralise some of its activities. It is known to reduce the contraction of collagen lattice by hypertrophic scar fibroblast (Zhang Z. et al (Burns) (2009) 35, 527-537. This is also described as a wound treatment agent in U.S. Pat. No. 5,510,328.

The use of gellan as a dressing allows the production of a dressing with improved mechanical properties over currently used materials such as alginates or cellulose based dressing, that is readily adaptable for the incorporation of biologically active materials/cells such as decorin, improved properties to allow the treatment of wounds, and which is readily scalable. Moreover, gellan has already been previously used within the food industry. Hence, the toxicity of the material is generally known, resulting in reduced potential regulatory issues regarding the use of this material.

The invention provides a dressing, such as a surgical or wound dressing, comprising a sheet of gellan gum. The sheet of gellan gum is typically 0.5-5 mm thick. It may comprise low acyl gum or high acyl gum, more typically low acyl gum.

The material typically comprises one or more biologically active additives. This may be an antifibrotic agent, such as an inhibitor of TGF-β. Such inhibitors are typically decorin, but may include other classes of anti-fibrotic agents such as antibodies or small molecules. One preparation of Decorin is also known by the proprietary name "Galacorin™".

Biologically active agents may also be selected from a cell, a dermal drug, a matrikine, a profibrotic agent, a pro-VEGF agent, an antibody, an antimicrobial agent and a proteoglycan.

Cells, such as stem cells, may be incorporated into the gellan gum. Stem cells include pluripotent and totipotent stem cells which may be derived from embryotic stem cells, or alternatively may be induced stem cells or other stem cells not derived from embryonic sources. The cells may be used to encourage new skin or bone growth, for example, or may produce trophic factors that stimulate endogenous repair cells.

Alternatively, cells may be attached to the surface of the dressing.

The surface of the dressing may be modified to allow the attachment of stem cells or, for example, proteins to the material. For example, the gellan membrane may be treated with sodium periodate to produce an oxidised membrane. This may be then further modified by treating with gelatin and sodium borohydride. This attaches gelatin via primary amide bonds. The gelatin introduces a RGD sequence which is a cell attachment site of a large number of adhesive extra cellular matrix, blood and cell surface proteins.

This may be used to attach, for example, meningiel fibroblasts MF or stem cells to the surface modified gellan. Such cells may also be incorporated within the gellan. Such cells advantageously give the property of providing cells for tissue regeneration or producing factors that stimulate endogenous repair cells. The stem cells are typically not derived from human embryos and are typically pluripotent.

The surface of the gellan may also be modified by the addition of one or more pro-scarring molecules such as TGF-β, bone morphogenic protein or FGF (fibroblast growth factor). This may be, for example, surface printed, on to a portion, especially a limited portion of the surface. This may be used to assist in adhering the wound dressing to an area of the wound or around the wound. In this way it is possible to have, for example, the wound dressing adhering around the outer regions of the wound, whilst still allowing the wound dressing to have anti-scarring capability over the major part of the wound, or a preselected area of the wound.

The dermal drug may be, for example, an analgesic. Analgesics include, for example, lidocaine, which may be used topically to relieve itching, burning and pain from skin inflammations or as a local anaesthetic. Fentanyl, which is a potent synthetic opioid analgesic, may also be used to treat pain, and may be used in combination with, for example, benzodiazepine.

The drug may also be a hormone. Hormones include, for example, estradiol, alone or in combination with, for example, norethidrone, levonorgestrel or norlgestromin. Additionally, ethenyl estradiol may also be used alone or in combination with those other compounds.

Other potential compounds include clonidinne, which acts as an $alpha_2$ adrenergic agonist and imidazoline receptor, which can be used to treat a wide range of symptoms, including withdrawal symptoms from narcotics, alcohol, benzodiazepine and nicotine and for use as a pain killer.

Scopolamine is also known as levo-duboisine. This is a tropane alkaloid drug with muscarinic antagonist effects, which may be used for, for example, to treat post-operative nausea, reduce gastrointestinal spasms, renal or biliary spasms and respiratory tract secretions.

Methyphenidate may be used. This acts as a dopamine reuptake inhibitor. It is manufactured and sold in the name of the trademark "Ritalin". Selegiline may be used, for example, in the treatment of diseases such as Parkinson's Disease and to alleviate the symptoms of Parkinson's Disease. Similarly, rotigotine, and rivastigmine may also be used.

Other compounds which may be used include heperan sulphate and hyaluronic acid, which may be useful in the production of cartilage augmentation. A number of protoglycans may also be used.

Matrikines may be incorporated into the dressing. Matrikines is a term relating to peptides obtained by proteolitic cleavage of constituents of the extracellular matrix. It has been shown, among other things, to elicit chemotaxis in a number of cell types. These include bioactive fragments of proteoglycans, glycosaminoglycans, heparin sulphate proteogylcans, collagen, tropoelastin, elastin, laminin-1, laminin-5, tenascin-C and fibronectin.

Profibrolitic agents, such as TGF-β may be incorporated within the matrix.

VEGF (vascular endothelial growth factor) is a single protein produced by cells that stimulates vasculogenesis and angiogenesis. Accordingly, vasculogenesis and angiogenesis may be controlled by inhibiting the EGF or the VEGF pathways, such as tyrosine kynases, such as by using tetrahydrocannabidiol or cannabidiol, lapatinib or cediranib. Anti-VEGF therapies are important in the treatment of certain cancers and maybe especially useful where, for example, the wound is the result of the removal of a cancer and it is important to try and inhibit and treat any residual cancer cells. Ranibizumaub is a monoclonal antibody fragment derived from bevacizumaub, which has been developed by Genetech for intraocular use, and in particular for neovascular age-related macular regeneration (Brown D. M. Ophthalmology 2008) 116(1) 57-65. This may be especially useful in the treatment of, for example, eye diseases.

A membrane may be used, for example, in combination with iontophoresis. This is a physical process in which ions flow diffusively in a membrane driven by an applied electric field. It drives a charged substance, such as a medication or bioactive agent, transdermally by repulsive electromotive force through the skin. A small current is applied to an iontophoretic chamber placed on the skin containing a charged active agent and its solvent vehicle. Another chamber or a skin electrode carries the return current. This may be used in combination with, for example, lidocaine and epinephrine, and fentanyl HCL.

The membranes may additionally be used in combination with lidocaine and tetracaine.

Antimicrobial agents include, for example, nanoparticles. Antimicrobials may be, for example, an antibacterial agent, such as an antibiotic or for example, nanoparticles of silver or copper.

Typically concentrations of the bioactive ingredients include decorin at a range of 1 to 30 μg/ml, typically 5-20 μg/ml The Applicant has found that the addition of a cross-linking agent may be used to alter or adjust the physical properties and include indeed the release properties of bioactive materials from the gellan to the wound.

Cross-linking agents include cations such as calcium and sodium, more typically calcium cations.

Typically the concentration of cations used is: 10-15 mM calcium chloride.

The properties of the gellan gum might be modified with one or more additional polymers. These may be used in the ratio of 90:10 to 50:50 wt %, typically 80:20, 70:30 and 60:40 (wt %) of gellan:polymer ratios were tested gellan:polymer. Polymers include, for example, gelatin and polyvinyl acetate (PVA). The PVA may be partially or fully saponified.

Typically the dressing may be obtainable by heating a mixture of 0.05 to 5 w/w % gellan gum in an aqueous liquid to form liquid gellan gum, and cooling the mixture in a mould to form a sheet of gellan gum. The liquid is typically a physiologically acceptable liquid, such as water, saline or a buffer such as phosphate buffered saline.

The surgical dressing may be dried after moulding. Typically before use, the dried moulding may then be rehydrated, for example by placing the dried dressing in an aqueous liquid such as that defined above, for 1-20 minutes, especially 2-20 or 10-20 minutes. Alternatively, the dried wound dressing may be rehydrated by simply placing the wound dressing on the wound. The wound exudate may then soak into the dried wound dressing.

Gellan sheet may also be used as a drug delivery medium. The transdermal sheet may simply contain one or more of the bioactive compounds as defined above. For example, nicotine may be included within the material and the gellan sheet may be used as a nicotine replacement patch. Alternatively, the gellan sheet may include, for example, decorin, which may be used on healed but scarred tissue, to assist in the removal and treatment of scarred tissue The invention also provides a method of treating an eye, wound, burn or surgical incision, comprising applying a dressing according to the invention to the eye, wound, burn or surgical incision. For example, this may be applied to the cornea of the eye, where the cornea is damaged, for example, by infection or surgery.

Surgical incision may be musculoskeletal. It may be incision in the brain, abdomen, socket of a tooth, a tendon or ligament, the skin or a wound, for example, from the treatment or removal or one or more tumours. That latter respect, the addition of more or more anti-tumour compounds within the material may be used to assist in removing residual cancer cells.

The invention also provides a dressing according to the invention for use in the treatment of an eye, a wound, a burn, a surgical incision or a cancer.

The wound treated may be caused by surgery, trauma, inflammation or infection.

The gellan sheet may be wrapped wound, for example, ligaments or tendons which have been surgically attached together. This may assist in not only preventing the ligament or tendons adhering to surrounding tissue, but, if suitable cells are incorporated within the gellan, or for example, BMP (bone morphogenic protein) protein is incorporated within the material, this may assist in the regrowth of material surrounding the ligament or to attach, for example, a ligament or tendon to bone.

A problem associated with implants, such as electrodes, pacemakers, biosensors and other implants, is that they often have cell growth on the surface of the implants, resulting in reduction in the function of the implant. A still further aspect of the invention provides placing a layer of gellan material, on a surface of the implant. The gellan gum may be as described above with the incorporation of, for example, one or more bioactive agents, such as one or more anti-scarring agents, such as decorin, together with other bioactive agents to modify local tissue responses to the implants. The implant may be selected from devices such as electrodes, a sensor, a pacemaker or a prosthetic bone or bone-like replacement material.

The invention further provides a bandage or sticking plaster comprising a layer of a dressing according to the invention. The bandage or sticking plaster may comprise, for example, an outer surface of, for example, a silicon material. It may also comprise an adhesive surround to the wound dressing to allow the wound dressing to be adhered to skin surrounding the wound.

A further aspect of the invention provides a method of making a dressing, such as a surgical wound dressing comprising:
(a) heating together 0.05-5% w/w gellan gum in an aqueous liquid, optionally with 0-5% % w/w of a further polymer to form a liquid gellan gum;
(b) cooling the liquid gellan gum;
(c) casting the gellan gum to form a sheet of gellan gum having a thickness of 0.5-5 mm thickness; and
(d) optionally drying the sheet of gellan gum.

The gellan gum may be dried, for example, at 37°.
The aqueous liquid may be, for example, water, saline or a buffer such as phosphate buffer saline as described above.
The process may additionally comprise the step of mixing the gellan gum and aqueous liquid at at least 80° C., most typically at least 90° C. or 100° C. to form liquid gellan gum.

The heated mixture may be cooled to, for example, 37° C. to 42° C. and one or more biologically active additives, such as those described above, may be incorporated into the cooled liquid gellan gum. This may be then allowed to set within the mould. Delaying adding one or more biologically active additives to the lower temperature helps prevent the degradation or loss of the activity of those additives.

Alternatively, the sheet of gel may be formed, for example, by extrusion of the gel.

The invention also provides methods of producing a surgical or wound dressing comprising a gellan gum and one or more biologically active additives, such as antifibrotic agents, comprising:
(a) spraying a layer of heated gellan gum onto a mould;
(b) depositing a layer of biologically active additive onto the layer of gellan gum;
(c) spraying a further layer of heated gellan gum onto the layer of biological additive; optionally repeating steps (b) and (c) one or more times; and
(d) optionally depositing a layer of biologically active additive on the final layer of gellan gum.

The Applicant found that cooling gellan gum to 40° C. produces a viscous liquid that reduces the ability to produce a substantially uniform layer of gel containing the biologically active agent. The gel needs to be cooled to reduce the risk of denaturing the additive.

The method improves the ability of produce the dressings. The gellan gum layer(s) may be cooled to, for example 40° C., prior to adding the layer of biologically active agent. Alternatively, the spraying of the gum cools the gel.

The biologically active agent may be dispersed in or dissolved in, a liquid such as water or buffer, prior to spraying onto the gel. Alternatively, it may be sprayed as a powder onto the layer of gel.

Each layer of gum may be, for example, 100 nm to 500 nm thick, specially 500 nm to 100 nm thick.

The biologically active agent, gel, additional polymer and/or final thickness of the dressing may be as described above.

A sheet of gellan gum may be hydrated with an aqueous liquid such as one of those defined above that may be endogenous or exogenous to the wound. Optionally, the aqueous liquid may comprise one or more biologically active additives.

Where the dressing is moist or wet, it may be compressed to exude at least a portion of liquid from the dressing. The exuded liquid may be removed, for example, by wicking the excess liquid away with, for example, blotting paper, and a liquid comprising one or more biologically active additives placed in contact with the dressing. The dressing may then be allowed to expand to draw the liquid containing the biologically active additive into the wound dressing. This allows, for example, a sheet of gellan gum without one or more biologically active additives to be produced and then packaged in a surgical packaging. Surgical packaging may then be removed, the dressing optionally rehydrated, and the biologically active additive may then be selected according to the type of use to which the dressing is intended to be used.

Biologically active additives may be as described above.

The cross-linking agent may optionally be added after the gellan gum has set in the mould. The cross-linking agent, such as a cation, including a calcium or sodium cation, may simply be pipetted onto the surface of the gellan gum, or alternatively the gellan gum may be placed in contact with, for example, a filter paper which has been moistened with the cross-linking agent. The cross-linking agent then diffuses into the gellan gum.

Cross-linking has been found to allow the release of biologically active compounds to be controlled.

It has also been noted that the dressings of the invention allow fluid from the wound or dressing, wound or burn for example, to pass through into the dressing. Fluid from the dressing may be analysed to check for, for example, infection or other analytes within the wound exudate that may be useful for clinical assessment/diagnosis/prognosis.

The invention will now be described by way of example only with reference to the following figures:

FIG. 3a shows the difference between gellan only and gellan cross-linked membranes. FIG. 3b shows the release from amniotic membrane.

MATERIAL AND METHODS

Industrial grade gellan was obtained from Kelco Limited (Surrey, United Kingdom) under the trade name Gelzan. Calcium chloride, and phosphate buffered saline (Dulbeccos A) were obtained from Sigma Aldridge Company, Dorset, United Kingdom. PETRI dishes, filter paper range (QL100-240 mm) and disposable 10 mm plastic syringes were obtained from Fisher Scientific, Loughborough, United Kingdom. The incubator used by an INCU-LINE, obtained from VWR, Sussex, United Kingdom.

2% w/w gellan hydrocolloid solution was prepared by weighing 2 grams of gellan powder using a calibrated balance. 98 ml of distilled water was measured and transferred to a glass bottle. Water was placed on a hot plate stirrer at 100° C. and 200 rpm. Gellan powder was added to the stirring water and left for four hours.

A 1% w/w calcium chloride solution was prepared by dissolving 1 gram of calcium chloride in 99 ml of distilled water.

The gellan hydrocolloid was stirred on a hot plate at 90° C. until the gellan became a liquid. This was then reduced to 40° C. 2.5 ml of gellan was syringed into a 55 mm petri dish using a plastic syringe. This was allowed to set for 15 minutes. To dehydrate the membrane sheet, the gel was placed in a 37° C. incubator for 6-8 hours.

To prepare a cross-linked sheet, the gelled gellan hydrocolloid was stirred on a hot plate at 90° C. at 200 rpm, until the gellan became liquid. This was reduced to 40° C. A filter paper was soaked in the calcium chloride solution and placed on the bottom of a petri dish. 2.5 ml of gellan was placed onto the filter paper using a plastic syringe. The gel was allowed to set for 5 minutes. A further filter paper soaked in the calcium chloride solution was placed on top of the set gel and left at room temperature for 15 minutes. The filter papers were then carefully removed and the membrane sheet was transferred into an incubator at 37° C. for 6-8 hours.

In order to rehydrate the sheets, the sheets were soaked in PBS for 2-3 minutes.

Figure 1:
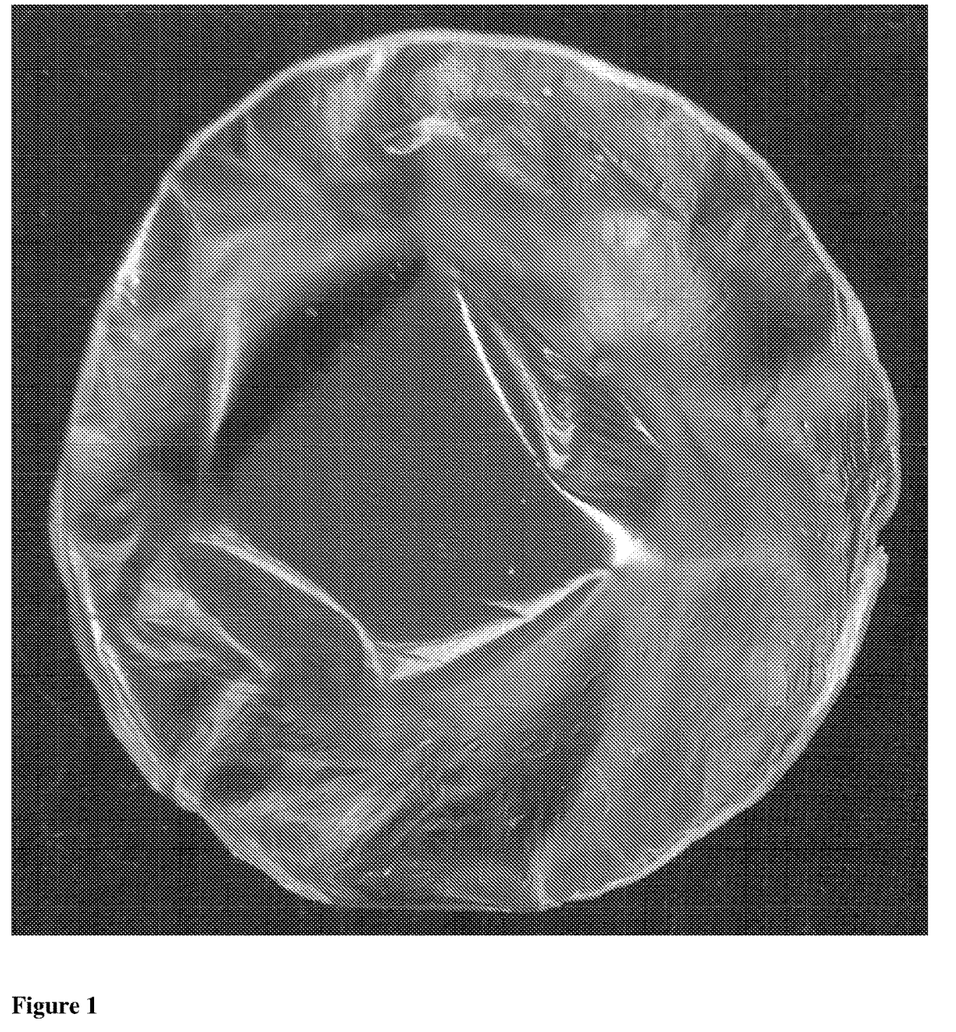
FIG. 1 shows a hydrogel dressing sheet manufactured according to the invention.

FIG. 1 shows an example of the dehydrated sheet.

The Effect of Various Calcium Chloride Concentrations on G' Gellan Membranes

Figure 2:
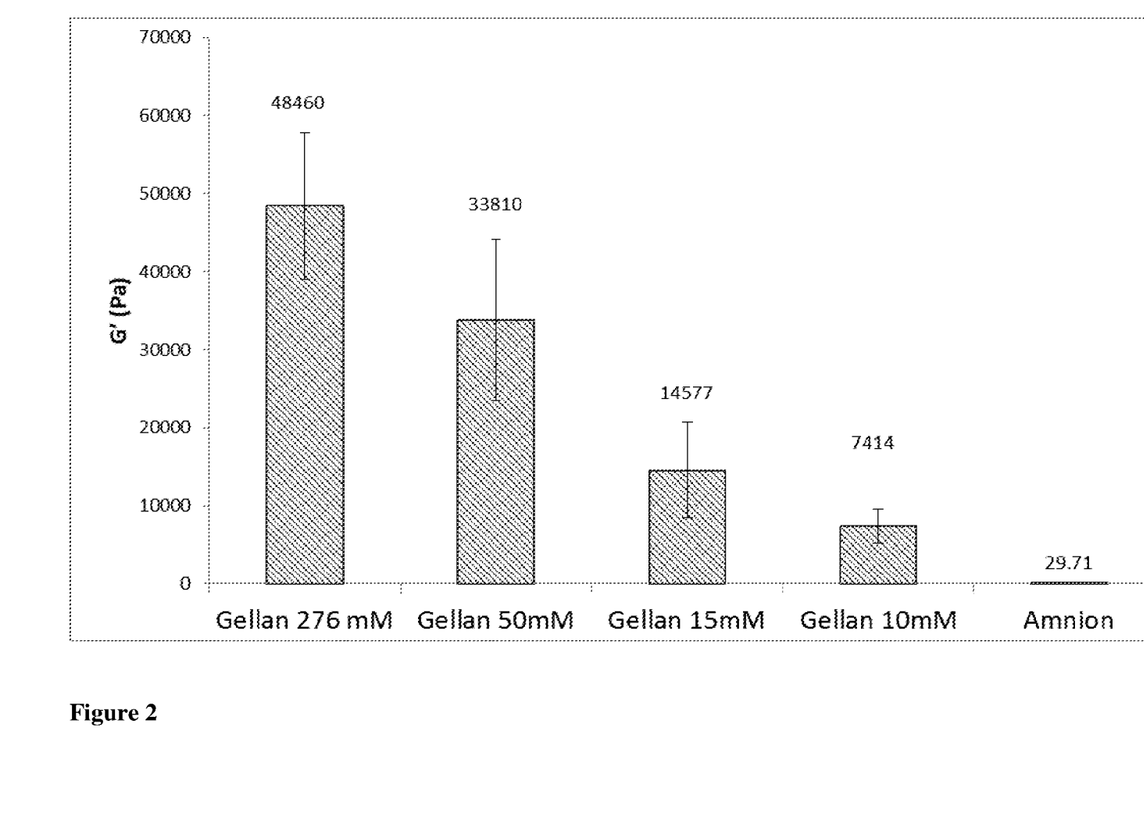
FIG. 2 shows the effect of a variety of calcium chloride concentrations on the G' of gellan membranes.

Gels were prepared with a range of different concentrations of calcium chloride. 276 mM calcium chloride, the gel was stiff, not easily drapable or easy to place around a wound. Gels prepared with 15 mM were shown to be more drapable around a spherical object, such as a marble, but were susceptible to tearing at maximum strain. 10 mM calcium chloride were more fragile and would tear more easily when lifted out of the mould. Therefore 15 mM calcium chloride was the preferred concentration to use. The effects on G' are shown in FIG. 2.

Figure 3:
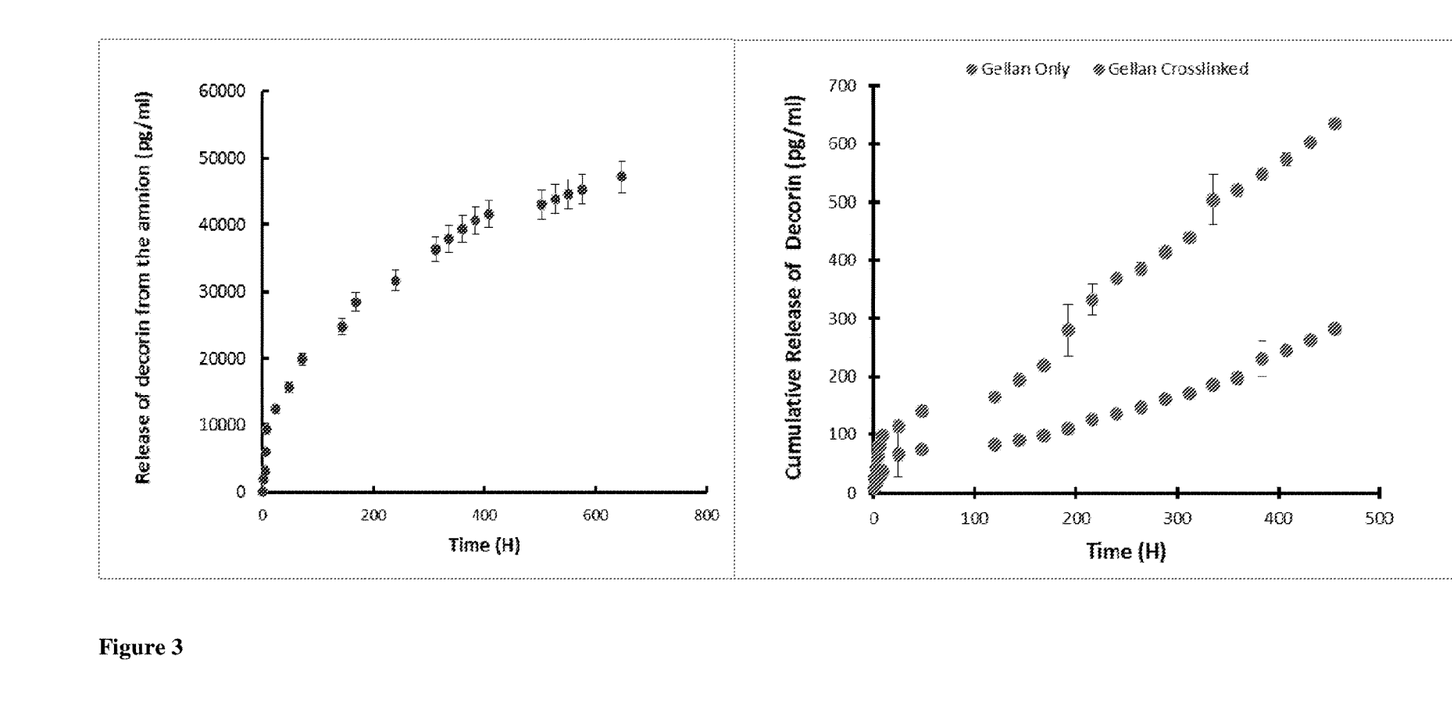
FIG. 3 compares the release of decorin, decorin from gellan membranes and amniotic membranes.
Figure 4:
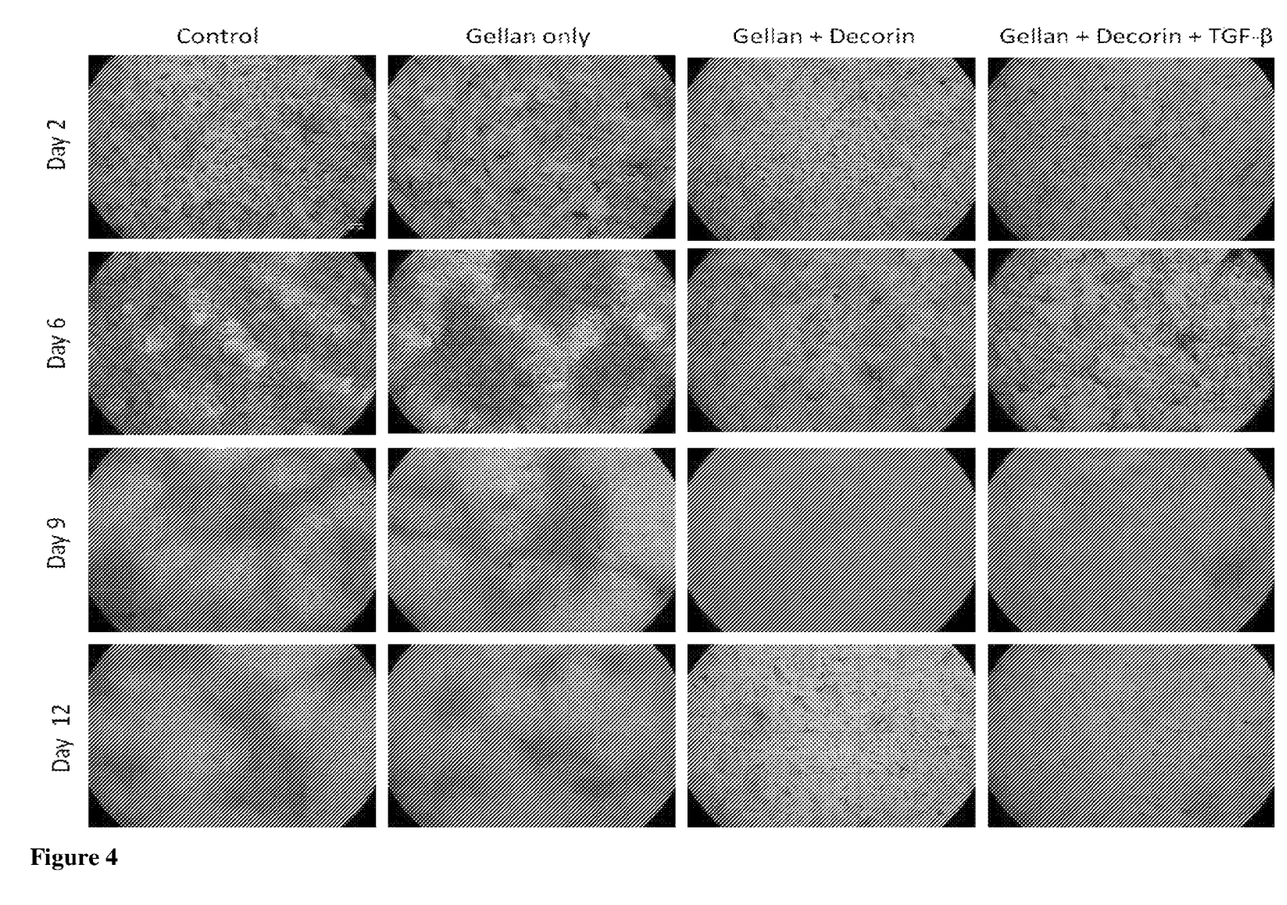
FIG. 4 shows an in vitro assessment of gellan membranes and shows the collagen deposition from MFs in the presence of gellan membranes, and, which have been assayed using sirius red.

FIG. 3 shows a comparison of the release of decorin from gellan membranes and amniotic membranes. Gellan-decorin membranes or amniotic membranes were placed in a release medium (Phosphate buffer saline, PBS) and placed in a shaker at 80 rpm at 37° C. Equal amounts of the release medium were taken at specific time intervals and equal amounts of fresh release medium were replaced to maintain a constant volume. The samples were analysed using a human decorin ELISA kit according to manufacturer's instructions FIG. 4—MFs were cultured in 6-well plates and left to attach overnight. After overnight attachment TGF-β1 was added to the cells to produces excess collagen. Decorin containing membranes were placed on top of the cultures and collagen production was observed using the Sirius Red assay over time.

Figure 5:
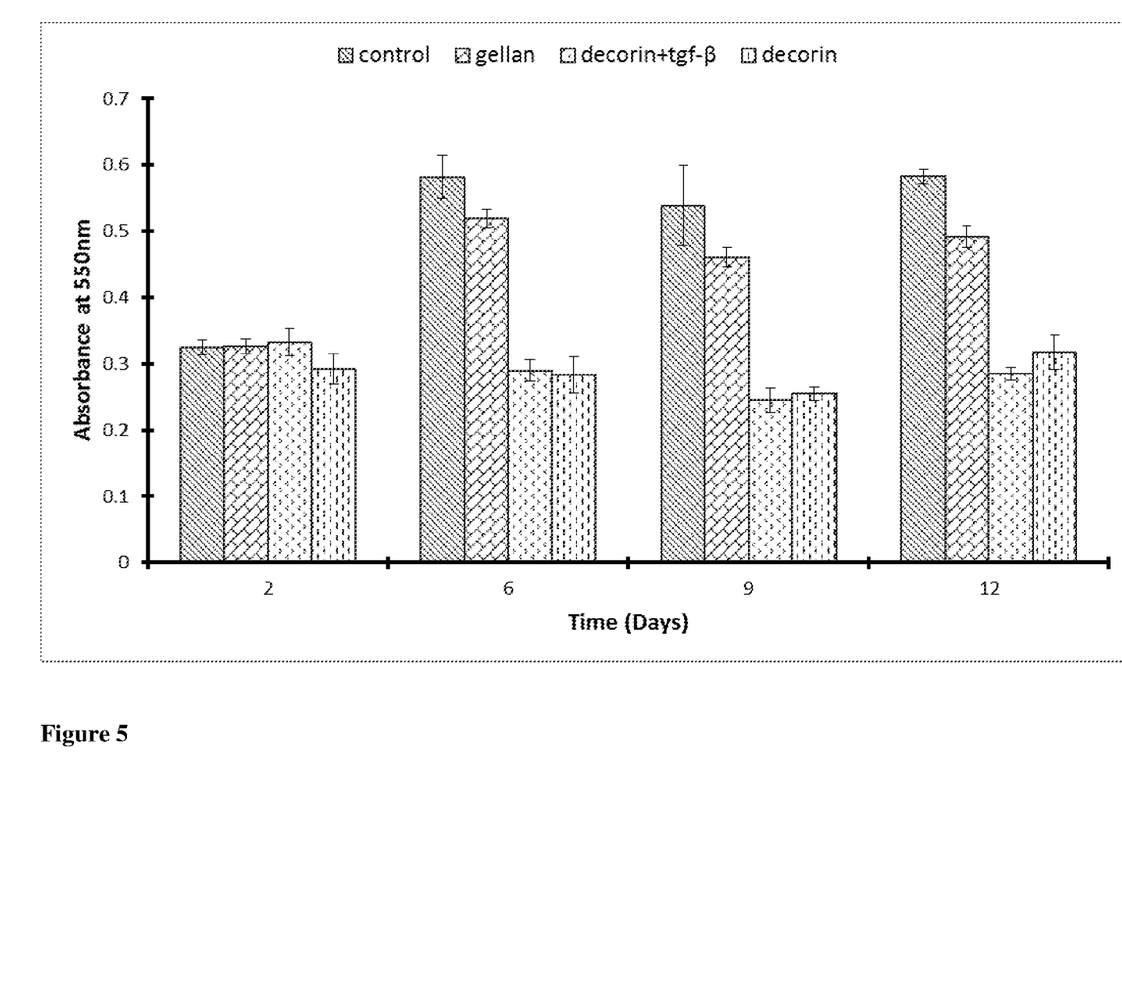
FIG. 5 shows that decorin significantly reduces the amount of collagen deposited over a 12 day period when compared to non-treated samples.

FIG. 5: For quantifying the amount of Sirius red dye bound to collagen in the cultures the Sirius red was dissolved with 0.1N sodium hydroxide and left on a shaker for 30 min at room temperature. The dissolved dye was measured colourimetrically using a plate reader at 550 nm FIG. 6: Gellan membranes were produced and cross-linked with 200 mM calcium chloride, and immersed in 10 mM sodium periodate solution for 2 h. The membranes were washed with PBS and further immersed in 10% (w/v) gelatin and 0.5% (v/v) $NaBH_4$. Furthermore the membranes were soaked overnight in EDC at 4° C.

Figure 6:
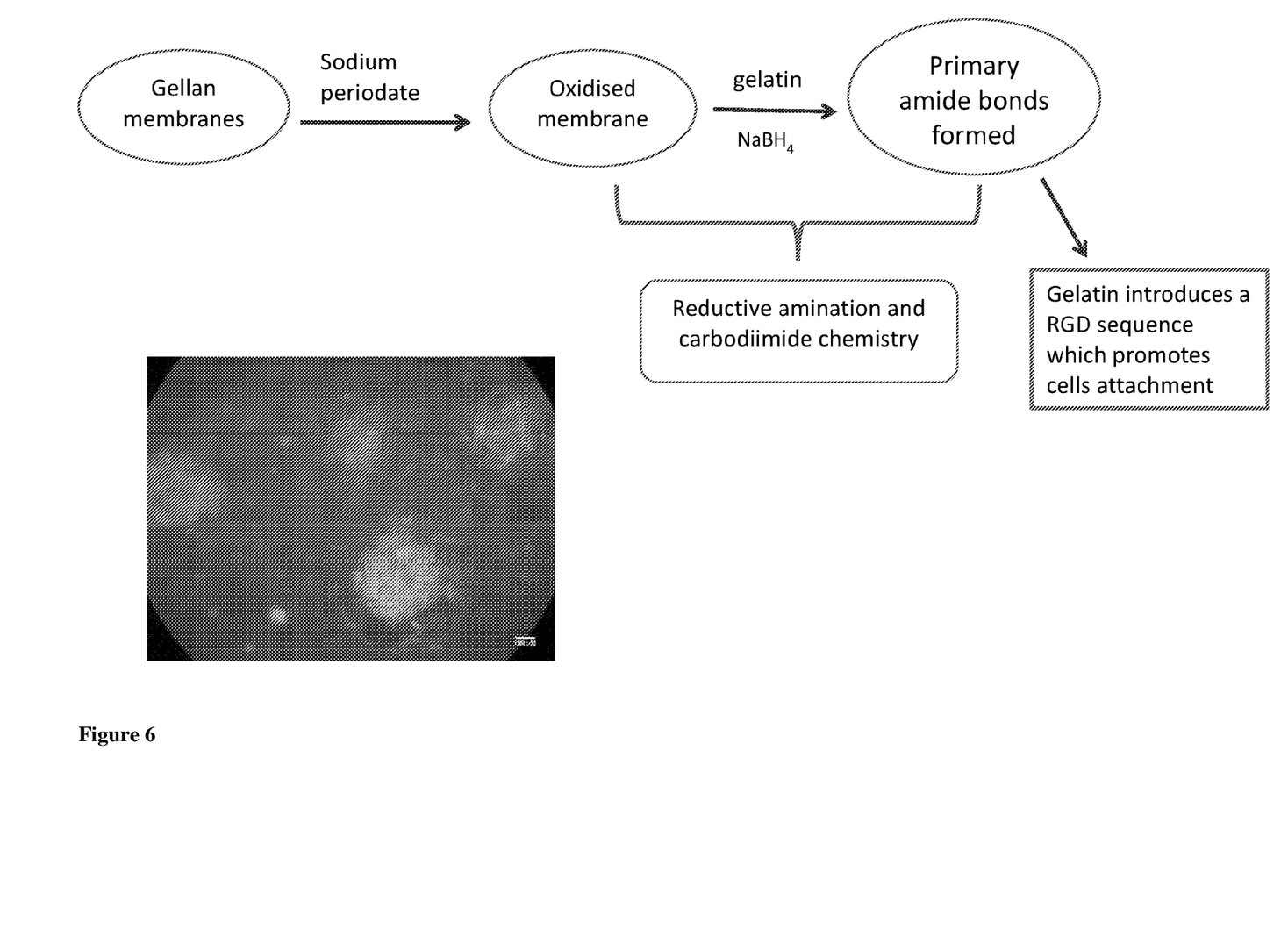
FIG. 6 shows a schematic diagram of the surface modification of gelatin to allow the attachment of MF cells.

To determine surface modification, MF cells were left to attach on the surface on membranes for 24 h and cell attachment was assessed using Calcein AM and Propidium Iodide staining.

Figure 7:
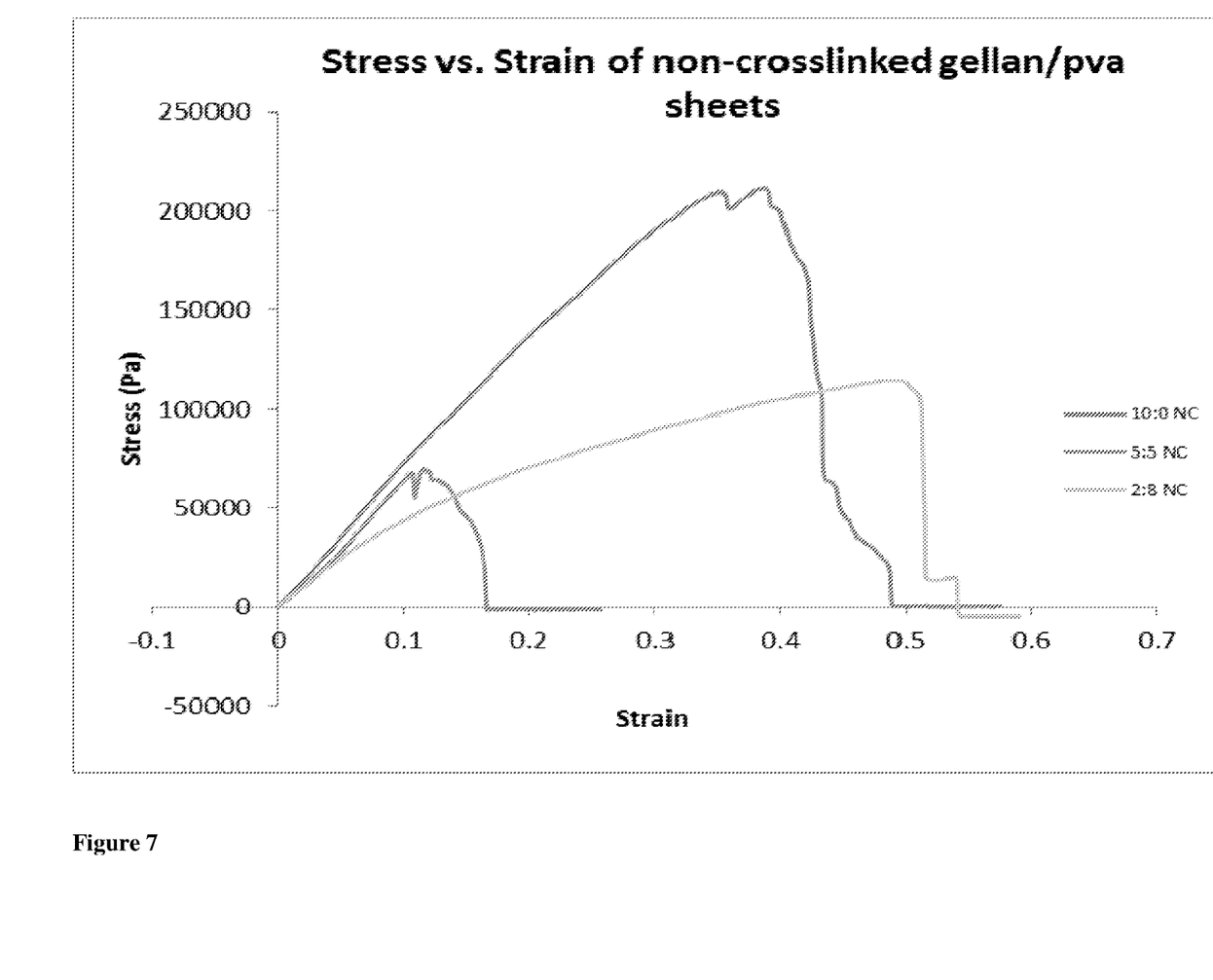
FIG. 7 shows the effect of adding PVA (polyvinyl alcohol) to gellan.

FIG. 7: Gellan membranes were produced with various amounts of PVA at 10:0, 50:50 and 20:80 (wt %) of gellan:polymer ratios. Tensile testing was carried out using a universal Instron machine to determine the physical properties of the gellan/PVA membranes Method of Spray Forming a Gel Dressing 2% w/w of gellan was dissolved in deionised water. A layer of the gellan gum at 60° C. was sprayed onto a mould. After spraying a layer of dextran blue, which was used as a substitute for decorin because it has similar properties and is visible to the naked eye, was sprayed onto the layer of gellan after a 5 second interval to allow the gellan to cool and gel. A 5 second interval was allowed prior to adding another layer of gellan gum and the process repeated 5 times. The whole process took approximately 40 seconds.

It was found that it was possible to form a structure with alternating layers of gellan and dextran blue, which was membrane-like. The advantage of this system is that it allows the material to be rapidly produced. Rastering the spray backwards and forwards across the surface allows a substantially even distribution of the material. Dextran blue was substantially evenly distributed within the gel dressing.

The advantage of this system is that it improves the ability to produce the dressing. It also lends itself to automation in that the spraying of the materials can be readily automated.

The invention claimed is:

1. A process for making a surgical, burn, or wound dressing, the process comprising:
    (a) heating about 2% to about 5% w/w gellan gum in a first aqueous liquid, and optionally about 5% w/w or less of a polymer, to form a liquid gellan gum;
    (b) cooling the liquid gellan gum;
    (c) adding one or more bioactive agents to the cooled liquid gellan gum;
    (d) casting the cooled liquid gellan gum to form a sheet having a thickness of about 0.5 mm to about 5 mm; and
    (e) drying the sheet; where the sheet is permeable, and where upon rehydration, the sheet is sufficiently transparent to allow a surgical incision, burn, or wound to be viewed.

2. The process of claim 1 further comprising mixing the gellan gum and aqueous liquid at about 80° C. or greater to form the liquid gellan gum.

3. The process of claim 1 wherein the liquid gum is cooled to about 37° C. to about 45° C.

4. The process of claim 1 wherein at least one of the one or more bioactive agents is an antifibrotic agent.

5. The process of claim 4 wherein the antifibrotic agent is added to the cooled liquid gellan gum at about 37° C. to about 45° C.

6. The process of claim 1 further comprising rehydrating the dried sheet with a second aqueous liquid, where the second aqueous liquid optionally comprises one or more bioactive agents.

7. The process of claim 6 further comprising compressing the rehydrated sheet to remove at least a portion of the second aqueous liquid from the sheet; and adding a third aqueous liquid comprising one or more bioactive agents, whereby the one or more bioactive agents are included in sheet.

8. The process of claim 7 wherein at least one of the one or more bioactive agents is selected from the group consisting of antifibrotic agents, pro-VEGF agents, anti-VEGF agents, antibacterial agents, and proteoglycans.

9. The process of claim 1 further comprising adding a cross linking agent to the gellan gum and the first aqueous liquid.

10. The process of claim 9 wherein the crosslinking agent is a cation.

11. The process of claim 1 wherein the additional polymer is gelatin or polyvinyl acetate, or a combination thereof.

12. The process of claim 11 wherein the polyvinyl acetate is partially or fully saponified.

13. The process of claim 1 wherein the dressing is configured to allow fluid to pass into the dressing.

14. The process of claim 1 wherein the dressing is configured to allow fluid to pass through the dressing.

15. A process for making surgical, burn, or wound dressing, the process comprising:
    (a) heating about 2% to about 5% w/w gellan gum in a first aqueous liquid, and optionally about 5% w/w or less of a polymer, to form a liquid gellan gum;
    (b) cooling the liquid gellan gum;
    (c) adding one or more bioactive agents to the cooled liquid gellan gum;
    (d) casting the cooled liquid gellan gum to form a sheet having a thickness of about 0.5 mm to about 5 mm; and
    (e) drying the sheet; where the sheet is hydratable, and where upon rehydration, the sheet is sufficiently transparent to allow a surgical incision, burn, or wound to be viewed.

16. The process of claim 15 wherein the liquid gum is cooled to about 37° C. to about 45° C.

17. The process of claim 15 wherein at least one of the one or more bioactive agents is an antifibrotic agent.

18. The process of claim 15 further comprising rehydrating the dried sheet with a second aqueous liquid, where the second aqueous liquid optionally comprises one or more bioactive agents.

19. The process of claim 15 further comprising adding a cross linking agent to the gellan gum and the first aqueous liquid.

20. The process of claim 15 wherein the additional polymer is gelatin or polyvinyl acetate, or a combination thereof.

* * * * *

UNITED STATES PATENT AND TRADEMARK OFFICE
CERTIFICATE OF CORRECTION

| | | |
|---|---|---|
| PATENT NO. | : 11,793,905 B2 | Page 1 of 1 |
| APPLICATION NO. | : 16/540142 | |
| DATED | : October 24, 2023 | |
| INVENTOR(S) | : Liam Grover et al. | |

It is certified that error appears in the above-identified patent and that said Letters Patent is hereby corrected as shown below:

In the Claims

Column 10 In Claim 15, Lines 24-25, "A process for making surgical, burn, or wound dressing" should read – A process for making a surgical, burn, or wound dressing –.

Signed and Sealed this
Fifth Day of December, 2023

Katherine Kelly Vidal
*Director of the United States Patent and Trademark Office*